(12) United States Patent
Cassels et al.

(10) Patent No.: US 6,797,485 B2
(45) Date of Patent: Sep. 28, 2004

(54) MASS SPECTROMETRY OF COLONIZATION FACTORS

(75) Inventors: Frederick J. Cassels, Ellicott City, MD (US); Lewis K. Pannell, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 287 days.

(21) Appl. No.: 09/942,974

(22) Filed: Aug. 31, 2001

(65) Prior Publication Data

US 2002/0106717 A1 Aug. 8, 2002

Related U.S. Application Data

(63) Continuation-in-part of application No. 09/580,385, filed on May 26, 2000, now abandoned, which is a continuation-in-part of application No. 09/070,802, filed on May 1, 1998, now abandoned.
(60) Provisional application No. 60/045,511, filed on May 2, 1997.

(51) Int. Cl.$^7$ ................................................. C12Q 1/24
(52) U.S. Cl. .............................. 435/30; 435/29; 435/34; 435/38

(58) Field of Search ................................. 435/7.3, 7.37, 435/8, 29, 30, 34, 38, 173.4, 173.7, 849

(56) References Cited

PUBLICATIONS

Cassels F. J. Absolute Molecular Weight Determination of *E. coli* Fimbrial Major Subunits. Abstracts of the 93$^{rd}$ General Meeting of the American Society for Microbiology. Presented May 16–20, 1993, p. 80 B–304.*

Jensen O. Direct Observation of UV Crosslinked Protein Nucleic Acid Complexes by MALDI. Rapid Comm in Mass Spectrometry 7(6)496–501, 1993.*

* cited by examiner

*Primary Examiner*—Ralph Gitomer
(74) *Attorney, Agent, or Firm*—Elizabeth Arwine

(57) ABSTRACT

Disclosed herein are methods for identifying at least one bacterial colonization factor of enterotoxigenic *E. coil* which comprise the following steps in the following order: 1) obtaining the colonization factor; 2) solubilizing the colonization factor by dissolving the colonization factor in 1,1,1,3,3,3-hexafluoro-2-propanol; 3) adding a solution of volatile acid to the solubilized colonization factor of step 2 to obtain a product; 4) subjecting the product of step 3 to mass spectrometry to determine the mass of the colonization factor; and 5) comparing the mass determined in step 4 with the mass of at least one known colonization factor.

11 Claims, No Drawings

US 6,797,485 B2

MASS SPECTROMETRY OF COLONIZATION FACTORS

CROSS REFERENCE TO RELATED APPLICATIONS

This application is a continuation-in-part of U.S. patent application Ser. No. 09/580,385, filed May 26, 2000, now abandoned, which is a continuation-in-part of U.S. patent application Ser. No. 09/070,802, filed May 1, 1998, abandoned, which takes priority from U.S. Provisional Patent Application Ser. No. 60/045,511, filed May 2, 1997, abandoned.

FIELD OF THE INVENTION

This invention relates to the use of mass spectrometry as a means for identifying specific colonization factors 9CF) in a sample of *E. coli*. The method is useful for tracking infections by differentially identifying the CF produced by specific organisms.

BACKGROUND OF THE INVENTION

Colonization factors (fimbriae, fibrillae or pili) are important virulence determinants of both intestinal and extra-intestinal *Escherichia coli*. For example, enterotoxigenic *E. coli* (ETEC), a major causative agent of diarrhea in children from and travelers to endemic regions, utilize CF for initial adherence necessary for colonization. However, the ability to detect and differentiate CF has been problematic, with incomplete CF data commonly being reported from field and survey studies. In addition, while efforts to clone and sequence *E. coli* CF have been underway for almost two decades, sequences of the same CF have been published with disagreement at several bases, indicating different amino acids at those positions. An independent means of verification of these sequences would be very valuable. This invention provides a technique of subunit mass determination that provides for the identification of *E. coli* CF as well as verification of sequence data.

The use of mass spectrometry for purposes of identifying colonization factors (CF) was first suggested by Cassels in an Abstract published in 1993. However, the methods suggested therein were not so effective as those under consideration in this disclosure, since the optimization achieved by following the steps taught herein provide increased efficiency and reliability.

SUMMARY OF THE INVENTION

Strains of ETEC and enteropathogenic *E. coli* (EPEC) were grown on agar or liquid broth, surface proteins removed, and CF detected by SDS-PAGE. Extracts containing sufficient amounts of CF were partially purified, with samples examined by electrospray mass spectrometry (MS) for mass determination of the CF subunit. In some cases N-terminal protein sequence (PSQ) of the subunit was obtained. In addition, purified CF from uropathogenic *E. coli* (P pili) were examined by MS. Results indicated that the use of MS gave a definitive identification of *E. coli* CF in almost all cases. Utilizing a simple process of growing ETEC strains, recovering CF, and purifying CF, 28 CF from 30 ETEC strains were identified. Overall eighteen different CF subunits were examined by MS. MS data for twelve CF subunits indicated agreement with published data (three validated one published sequence over another), and six of the CF are not yet sequenced.

The data clearly shows that mass spectrometry provides for identification of CF from ETEC strains grown in a simple standardized procedure. Moreover, MS data can be used to verify sequencing data of *E. coli* CF, as well as give the mass of unsequenced CF for future comparison. The resolving power of MS is such that the structural subunits of *E. coli* CF are differentiable, with protein sequencing providing valuable confirmatory information.

The preferred process for identifying bacterial colonizing factors in a culture comprises the steps of:
1) suspending bacteria in an isotonic solution, followed by heating for 15 to 30 minutes at a temperature sufficient to release the colonization factors into solution,
2) centrifuging the product obtained in step 1, then discarding the precipitate obtained after centrifugation while retaining the supernatant,
3) adding sufficient ammonium sulfate to the supernatant obtained in step 2 to obtain a concentration of 15% to 50% saturation of ammonium sulfate until a precipitate is seen,
4) centrifuging the product of step 3 containing the precipitate to pelletize the precipitate,
5) dissolving the pellet obtained in step 4 in water and dialyzing to remove ammonium sulfate and other small molecules and retaining the material remaining inside the dialysis membrane,
6) drying the product retained in the dialysis membrane in step 5 to obtain dried colonization factor,
7) solubilizing the dried colonization factor obtained in step 6 by first dissolving in 1,1,1,3,3,3-hexafluoro-2-propanol, then adding a volatile acid in aqueous solution to provide solubilized colonization factor,
8) subjecting solution containing solubilized colonization factor obtained in step 7 to mass spectrometry to determine mass, and comparing mass of proteins found therein with mass of known colonization factors.

DESCRIPTION OF THE INVENTION

Diarrhea has always been a major cause of illness and death, especially among the very young and very old, in tropical and subtropical climates, particularly in developing countries. In addition, travelers to these countries are at risk. It is the purpose of this invention to provide important information useful for identifying particular strains of infectious organisms. Toward this end, several organisms have been studied. The identification of colonization factor (CF) and subsequent exposure of CF to spectrometry has proven very useful.

Mass spectrometry has been used to characterize all manner of organic molecules. Recent advances in mass spectrometry have allowed its use on large molecules, especially proteins. Because the masses of individual amino acids vary(except leucine and isoleucine), masses of polypeptides often are unique. Electro-spray mass spectrometry has been shown to be useful and extremely accurate (about 1 mass unit/10,000 MW) to a total mass of 30–40 kD. Data clearly shows that use of electrospray mass spectrometry and protein sequencing as applied to the identification of ETEC CF.

The bacteria were grown on regular agar and on agar supplemented with bile salts. The preferred process of the invention is practiced using the following steps:
1) Bacteria are suspended in an isotonic solution, then heated for about 20 minutes at about 65° C.
2) The product of step 1 is centrifuged and the precipitated material is discarded.
3) Supernatant obtained in step 2 is run on a SDS-PAGE gel.
4) If a prominent band in the 14–20 kD range is seen, the supernatant is processed in the following manner:

5) To the supernatant of step 2, ammonium sulfate is added to 20% saturation.

6) The product of step 5 is centrifuged to pelletize the precipitate.

7) The product of step 6 is put into solution and the resulting material is dialyzed to remove the ammonium sulfate, sodium chloride and other smaller molecules such as salts and peptides. (This product may be applied to an SDS-PAGE gel to evaluate purity). The dialyzed residue containing CF is dried, then solubilized.

8) The product of step 7 is subjected to mass spectrometry.

The method presents several advantages over prior art methods. It is not necessary to fully purify the colonization factor before analysis. Some of the samples were less than 35% pure. Many samples were less than 50% pure. Furthermore, using the methods of the invention, it is possible to identify the presence of more than one factor in a sample. As many as three colonization factors have been found in a single sample. Using means of the invention, it is possible to trace infections.

Materials and Methods

Thirty ETEC strains were grown and prepared for analysis.

Bacteria were suspended in 9% NaCl solution, then heated for about 20 minutes at about 65° C. (A range of 15–30 minutes at 50° to 70° C. would be appropriate.) This resulting material was then centrifuged and the supernatant was run on SDS-PAGE gels. It was expected a prominent protein band would be seen at approximately the 15 kD range on the gel if colonization factor was expressed by the bacteria. Furthermore, the approximate purity of the CF can be determined from the SDS-PAGE gel. Yield was estimated and expressed in mg. The purity was estimated and expressed as percentage of CF relative to the total protein.

The heating at 50° to 70° C. in solution is required to cause release of the CFs. While the time and temperature may vary, best results were obtained by heating for about 20 minutes at a temperature of about 65° C.

The organisms were grown on two substrates—one containing bile and the other without bile salts. Samples which demonstrated a reasonable yield and purity of CF were further processed by addition of ammonium sulfate to the 20% level of saturation. This material was subjected to centrifugation to obtain a pellet. Ammonium sulfate (AS) was then added to the supernatant in sufficient amounts to obtain 40% saturation. This material was then centrifuged to obtain a second pellet. As a general principal, use of ammonium sulfate in concentration of 15% to 50% are usable. However, it was found that the concentration of 20% to 40% was generally advantageous, with some CF's being more easily pelletized at about 20% AS concentration, while others were more easily pelletized at about 40% AS concentration.

Each of the pellets were then suspended. The supernatants containing 40% saturation of ammonium sulfate (AS) and each suspension containing the pellets were dialyzed to remove AS and NaCl. All three samples (suspended pellets from 20% and 40% AS saturation, and the supernatant from the 40% AS saturation) were run on SDS-PAGE gels and the yield determined. In all but one instance, the highest purity and yield were seen using the precipitate from the pellet obtained by centrifugation of the sample containing 20% saturation of AS.

The solubilization of the colonization factors was essential for obtaining optimum results. Samples were dissolved in 1,1,1,3,3,3-hexafluoro-2-propanol (sold by Sigma under product #H8508) to a concentration of about 10–20 $\mu$M. Once the factors were fully solubilized, an equal volume of 5% acetic acid in water was added to bring the protein concentration to 5–10 $\mu$M. The samples were infused into the electrospray source at a rate of 0.6 $\mu$L per minute. The mass spectrometer was typically scanned from m/z 1400 to m/z 2500 continuously every 40 seconds and mass spectra from runs summed. Electrospray mass spectra were run on a JEOL SX102 (Japan) mass spectrometer equipped with an Analytica (Bradford, Conn.) electrospray source with heated capillary (125C.). The spectrum acquired (m/z) was deconvoluted with the JEOL software and the "mass" spectrum obtained which revealed the presence of the proteins. Volatile acids other than acetic acid may be used. It is important that the acid used should not form a salt.

The strains evaluated using the methods of the invention encompassed three groups of strains. One group of strains appeared to possess colonization factors in combinations not normally found as screened by monoclonal antibody means. These included strains known as 044210, 041421, PDAS40-1, H545A, H1024A and H503A. A second group was obtained from Egypt. These strains have been identified as strains C95-1059, C9503808a, C95-9303E, C95-106039D, C95-12335A and C95-16080A. These strains were obtained from collaborators in the Navy who were conducting field surveys of children with diarrhea in rural villages near Alexandria, Egypt. These strains appeared to contain a previously undescribed colonization factor, or were positive for more than one anti-colonization factor monoclonal antibody. A third group identified as DS168-1 and DS 26-1 were obtained from U.S. soldiers in Saudi Arabia during Desert Shield/Desert Storm who suffered from diarrhea. The streamlined growth, purification and sample preparation procedures disclosed herein were found to be relatively simple and proved quite successful in characterizing the CF of these groups. The following strains were studied:

| Strain | Toxin | Origin | Antibody profile |
|---|---|---|---|
| STUDY STRAINS | | | |
| Egyptian and Saudi | | | |
| C95-1059 | ST | Egypt | CS19 |
| C95-3808A | LTST | Egypt | CS19 |
| C95-9303E | LT | Egypt | CS17 |
| C95-16039D | LTST | Egypt | CS1 |
| C95-12335A | ST | Egypt | CS1, CS3 |
| C95-16080A | ST | Egypt | CS1, CS3 |
| DS168-1 | LT | Saudi Arabia | CS17-like |
| DS26-1 | LT | Saudi Arabia | CS17-like |
| Unusual CF Stains | | | |
| 044210 | LT | Mexico | CFA/III, CS17 |
| 041421 | ST | Mexico | CFA/IV, CS7 |
| 028935 | LTST | Mexico | CFA/II, CFA/IV |
| PDAS40-1 | LT | Brazil | CS7, CFA/IV |
| H545A | LT | India | CFA/III, CS17 |
| H1024A | ST | India | CFA/IV, PCF O166 |
| H503A | ST | India | CFA/IV, PCF O166 |
| E2528C1 | LT | Cruise ship | CFA/III, PCFO166 |

[1]By monoclonal antibody, except DS168-1 and DS26-1 (polyclonal)

The following data relates to the growth and expression of ETEC colonization factors as indicated below.

GROWTH AND EXPRESSION OF ETEC COLONIZATION FACTORS

| Strain | Media | Yield (mg)/% Purity | Preferred Media | Ammon Sulfate | Yield (mg)/% purity | CF |
|---|---|---|---|---|---|---|
| *1A. Egyptian and Saudi Strains* | | | | | | |
| C95-1059 | CFA bile | 2.2/50% | CFA bile | 20% | 1.2/83% | CS19 |
| C95-3808A | CFA bile | 6.6/50% | CFA bile | 20% | 1.4/75% | CS19 |
| C95-9303E | CFA bile | 0.5/10% | CFA bile | 20% | 0.14/33% | CS17 |
| C95-16039D | CFA bile | 3.8/30% | CFA bile | 20% | 0.6/55% | O166 |
| C95-12335A | CFA | 4.2/35% | | 40% | 5.2/90% | |
| | CFA bile | 7.0/35% | | 20% | 3.1/80% | CS1, CS3, CS3a |
| C95-16080A | CFA | 1 nx | | | | |
| | CFA bile | 1 nx | | | | |
| DS 168-1 | CFA bile | 5.0/33% | CFA bile | 20% | 1.5/75% | CS19 |
| DS 26-1 | CFA bile | 5.4/40% | CFA bile | 20% | 0.7/60% | CS19 |
| DS 37-4 | CFA bile | 1 nx | | | | |
| | CFA | 1 nx | | | | |
| *B. Unusual Combination CF Strains* | | | | | | |
| 044210 | CFA bile | 9.15/70% | CFA bile | 20% | 2.1/90% | CS17 |
| 041421 | CFA bile | 5.9/25% | CFA bile | 20% | 0.57/50% | CS5 |
| 028935 | CFA bile | 1.9/5% | | 40% | 0.14/10% | PCF 0166 |
| PDAS40-1 | CFA bile | 4.6/45% | CFA bile | 20% | 0.86/60% | PCF 0166 |
| | | | | 40% | 1.4/75% | |
| H545A | CFA bile | 3.4/65% | CFA bile | 20% | 0.88/78% | CS17 |
| H1024A | CFA bile | 3.9/33% | CFA bile | 20% | 0.58/80% | PCF 0166 |
| H503A | CFA bile | 1.6/20% | CFA bile | 20% | 0.35/28% | PCF 0166 |
| E2528C1 | CFA | 3.1/50% | CFA | 20% | 1.2/90% | CFA/III |
| | CFA bile | 1.9/18% | | 20% | 0.4/33% | |
| *C. Well Characterized Strains* | | | | | | |
| E20738A | CFA bile | 26.1/35% | CFA bile | 20% | 3.7/90% | CS17 |
| E8775 | CFA bile | 8.8/15% | | 20% | 2.8/70% | CS4 |
| | CFA | 9.6/15% | | 20% | 1.4/70% | |
| C91f | CFA bile | 14.7/25% | CFA bile | 20% | 3.2/80% | CS2 |
| | CFA | 30.4/25% | | 20% | 1.8/80% | CS2 |
| 350 C1A | CFA bile | 42/70% | CFA bile | 20% | 17/90% | PCFO159 |
| D02-2 | CFA bile | 15.4/25% | CFA bile | 20% | 6.1/65% | CS7 |

The expected mass of the colonization factors have been studied and published. The expected and experimentally determined masses were compared and the following data was obtained:

| Colonization Factor | Mass Expected | Experimental Mass |
|---|---|---|
| CFA/I | 15,074.1 | 15,076.6 |
| | 15,046.1 | |
| | 15,057.2 | |
| CS1 | 15,246.2 | 15,241.4 |
| CS2 | 15,418.7 | 15,420.6 |
| CS3 | 15,111.5 | 15,112.1 |
| | 15,079.7 | |
| CS3a | unknown | 15,241.4 |
| CS4 | 14,958.8 | 14,960.8 |
| CS5 | 18,617 | 18,620.6 |
| CS6a | 15,057.9 | 15,055.1 |
| | 15,070.8 | |
| CS6b | 15,877.4 | 15,876.8 |
| | 15,132.7 | |
| CS7 | unknown | 18,725.6 |
| CS17 | 15,374.8 | 15,376.8 |
| CS19 | 14,963.5 | 14,964.9 |
| CFA/III | 21,607.6 | 21,623.1 |
| PCF O159 | unknown | 17,921.4 |
| PCF O166a | 14,987.8 | 15,028.9 |
| PCF O166b | 15,541.4 | 15,539.1 |
| AF/R1 | 16,526.5 | 16,526.5 |
| | 14,401.4 | |
| Pap | 16,554.3 | 16,555.3 |

Relying on the spectrographic data, the following conclusions would have been drawn:

| Strain | Antibody Data | Mass Spec Conclusion | PSQ Conclusion |
|---|---|---|---|
| ETEC: EGYPTIAN AND SAUDI STRAINS | | | |
| Egyptian village: | | | |
| C95-1059 | CS19 | CS19 | CS17 or CS19 |
| C95-3808A | CS19 | CS19 | |
| C95-9303E | CS17 | CS17 | |
| C95-16039D3 | CS1 | PCFO166 | PCFO166 |
| C95-12335A | CS1, CS3 | CS1, CS3, CS3a | CS3, CS3a |
| C95-16080A | CS1, CS3 | l.n.x. | |

-continued

| Strain | Antibody Data | Mass Spec Conclusion | PSQ Conclusion |
|---|---|---|---|
| US Soldiers in Saudi Arabia | | | |
| DS 168-1 | CS17-like | CS19 | |
| DS 26-1 | CS17-like | CS19 | |
| DS37-4 | CS17 | l.n.x. | |
| ETEC: UNUSUAL CF STRAINS | | | |
| 044210 | CFA/III, CS17 | CS17 | CS17 or CS19 |
| 041421 | CFA/IV, CS7 | CS5 | CS5 |
| 028935 | CFA/II, CFA/IV | PCF O166 and CS5 | |
| PDAS40-1 | CS7, CFA/IV | PCF O166 and CS7 | |
| H545A | CFA/III, CS17 | CS17 | CS17, CS19 |
| H1024A | CFA/IV, PCF0166 | PCF O166 | |
| H503A | CFA/IV, PCF0166 | PCF O166 | |
| E2528C1 | CFA/III, PCF0166 | CFA/III | |
| ETEC: WELL CHARACTERIZED STRAINS | | | |
| ETEC Strains: | | | |
| H10407NM | CFA/I | CFA/I | CFA/I |
| E20738A | CS17 | CS17 | |
| E8775 | CS4, CS6 | CS4 | CS4, CS6 |
| C91f | CS2 | CS2 | CS2 |
| 350C1A | PCFO159 | PCF O159 | |
| D02-2 | CS7 | CS7 | CS7 |
| M346 | CS6 | CS6 | CS6 |
| Z26-5 | CFA/III | CFA/III | |
| E17018A | CS5, CS6 | CS5 | |
| 60R75 | CS1 | CS1 | CS1 |
| LP97-009 | CS3 | CS3 | |
| LP97-020 | CS17 | CS17 | |
| LP97-021 | CS17 | CS17 | |
| Non-ETEC Strains: | | | |
| RDEC-1 | AF/R1 | AF/R1 | AF/R1 |
| HB101/ pPAP15 | Pap | Pap | | l.n.x. - little to no expression of colonization factor

From the above, it is shown that using the methods of the invention 28 of 30 ETEC strains investigated in this study produced enough CF for further purification and analysis. The method of the invention provides better production (based on yield and purity) of CF on CF agar with 0.15% bile salts was seen in 26 of 28 strains. Growth of strains E2528C1 (CFA/II-I) and 60R75 (CS1), on CF agar alone resulted in better production of CF.

Masses of the CF from 28 strains were determined, compared to known masses of CF, with most identified by their masses alone in a manner that was more rapid and cost effective than previously used methods.

The N-terminal protein sequence was obtained for twelve CF. However, while protein sequence data was useful, it was not definitive in identification of CF.

The methods of the invention may be used in conjunction with other methods to identify ETEC strains.

What we claim is:

1. A process for identifying bacterial colonization factors in a culture of enterotoxigenic *E. coli* bacteria comprising the steps of:
  1) suspending bacteria in an isotonic solution, followed by heating for 15 to 30 minutes at a temperature sufficient to release the colonization factors into solution,
  2) centrifuging the product obtained in step 1, the discarding the precipitate obtained after centrifugation while retaining the supernatant,
  3) adding sufficient ammonium sulfate to the supernatant obtained in step 2 to obtain a concentration of 13% to 50% saturation of ammonium sulfate until a precipitate is seen,
  4) centrifuging the product of step 3 containing the precipitate to palletize the precipitate,
  5) dissolving the pellet obtained in step 4 in water and dialyzing to remove ammonium sulfate and other small molecules and retaining the material remaining inside the dialysis membrane,
  6) drying the product retained in the dialysis membrane in step 5 to obtain dried colonization factor,
  7) solubilizing the dried colonization factor obtained in step 6 by first dissolving in 1,1,1,3,3,3-hexafluoro-2-propanol, then adding a volatile acid in aqueous solution to provide solubilized colonization factor,
  8) subjecting solution containing solubilized colonization factor obtained in step 7 to mass spectrometry to determine mass, and comparing mass of proteins found therein with mass of known colonization factors.

2. A method of solubilizing colonization factor comprising the steps of
  1) dissolving the colonization factor in 1,1,1,3,3,3-hexafluoro-2-propanol, then
  2) adding the acidified aqueous solution which has been acidified with a volatile acid to the composition obtained in step 1.

3. A method of claim 2 wherein the volatile acid is acetic acid.

4. A method of claim 1 wherein, in step 1, the bacteria in isotonic solution is heated for about 20 minutes at about 65° C.

5. A method of claim 1 wherein the colonization factor is solubilized before subjection to mass spectrometry by dissolving in 1,1,1,3,3,3-hexafluoro-2-propanol followed by addition of an acid in aqueous solution.

6. A method of claim 1 wherein, in step 8, the solution is scanned at m/z 1400 to m/z 2500.

7. A method for identifying at least one bacterial colonization factor of enterotoxigenic *E. coli* which comprises the following steps in the following order:
  1) obtaining the colonization factor;
  2) solubilizing the colonization factor by dissolving the colonization factor in 1,1,1,3,3,3-hexafluoro-2-propanol;
  3) adding a solution of volatile acid to the solubilized colonization factor of step 2 to obtain a product;
  4) subjecting the product of step 3 to mass spectrometry to determine the mass of the colonization factor; and
  5) comparing the mass determined in step 4 with the mass of at least one known colonization factor.

8. The method of claim 7, wherein the colonization factor is dissolved in 1,1,1,3,3,3-hexafluoro-2-propanol to a concentration of about 10 $\mu$M to about 20 $\mu$M.

9. The method of claim 7, wherein the volatile acid is acetic acid.

10. The method of claim 9, wherein the acetic acid solution was added to bring the concentration to 5 $\mu$M to 10 $\mu$M.

11. The method of claim 7, wherein the product is scanned m/z 1400 to m/z 2500.

* * * * *